(12) United States Patent
Chimenti et al.

(10) Patent No.: US 9,354,183 B2
(45) Date of Patent: May 31, 2016

(54) METHOD TO OPTIMIZE RUN LENGTHS AND PRODUCT QUALITY IN COKING PROCESSES AND SYSTEM FOR PERFORMING THE SAME

(71) Applicants: Robert J. Chimenti, Short Hills, NJ (US); Brian D. Albert, Fairfax, VA (US); Berne K. Stober, Esmont, VA (US); Christopher J. Wolfe, Alexandria, VA (US)

(72) Inventors: Robert J. Chimenti, Short Hills, NJ (US); Brian D. Albert, Fairfax, VA (US); Berne K. Stober, Esmont, VA (US); Christopher J. Wolfe, Alexandria, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 411 days.

(21) Appl. No.: 13/868,344

(22) Filed: Apr. 23, 2013

(65) Prior Publication Data

US 2014/0311953 A1 Oct. 23, 2014

Related U.S. Application Data

(60) Provisional application No. 61/642,023, filed on May 3, 2012.

(51) Int. Cl.
*G01N 21/65* (2006.01)
*G01N 21/94* (2006.01)
(Continued)

(52) U.S. Cl.
CPC .............. *G01N 21/94* (2013.01); *C10G 75/00* (2013.01); *G01N 21/64* (2013.01); *G01N 21/65* (2013.01); *G01N 2201/08* (2013.01)

(58) Field of Classification Search
CPC ....... C10G 75/00; G01N 21/64; G01N 21/65; G01N 21/94; G01N 2201/08
See application file for complete search history.

(56) References Cited

U.S. PATENT DOCUMENTS 2,294,719 A * 9/1942 Court ................... C10B 33/006
                                                        239/244
3,825,081 A    7/1974 McMahon
4,220,518 A    9/1980 Uchida et al.
(Continued)

FOREIGN PATENT DOCUMENTS

EP         0053227 A1    6/1982
JP        60-158289 A    8/1985
WO       2008045609 A2   4/2008

OTHER PUBLICATIONS

PCT Search Report issued in corresponding PCT Application No. PCT/US2013/038780 on Jul. 15, 2013 (4 pp.).
(Continued)

*Primary Examiner* — Renee E Robinson
*Assistant Examiner* — Derek Mueller
(74) *Attorney, Agent, or Firm* — Glenn R. Barrett; Chad A. Guice (57) ABSTRACT

System to detect coking in at least one component of refinery equipment is provided. The system includes a fiber optic assembly having at least one optical fiber operably coupled with the component, the fiber optic assembly further including a light source to transmit light having a known parameter through the optical fiber and a receiver to receive the light from the optical fiber, and a processor in communication with the fiber optic assembly to identify a shift in the parameter received by the receiver, the shift corresponding to an operating characteristic of the component. Method also provided for detecting coking using the system to detect coking disclosed herein.

24 Claims, 5 Drawing Sheets

(51) Int. Cl.
*C10G 75/00* (2006.01)
*G01N 21/64* (2006.01)

(56) References Cited

U.S. PATENT DOCUMENTS

| | | | |
|---|---|---|---|
| 4,294,803 | A | 10/1981 | Uchida et al. |
| 4,402,790 | A | 9/1983 | Lynn et al. |
| 4,617,638 | A | 10/1986 | Krause et al. |
| 5,190,634 | A | 3/1993 | Fernandez-Baujin et al. |
| 5,410,988 | A | 5/1995 | Miyama et al. |
| 6,270,656 | B1 | 8/2001 | Gibson et al. |
| 6,533,922 | B2 | 3/2003 | Siskin et al. |
| 7,515,781 | B2 * | 4/2009 | Chimenti ............... G01L 1/246 385/12 |
| 7,922,896 | B2 | 4/2011 | Newman et al. |
| 7,951,340 | B2 | 5/2011 | Brons et al. |
| 2007/0019898 | A1 | 1/2007 | Chimenti et al. |
| 2007/0038393 | A1 | 2/2007 | Borah et al. |
| 2008/0128323 | A1 * | 6/2008 | McCoy ............... C10G 9/002 208/44 |
| 2008/0185316 | A1 | 8/2008 | Respini et al. |
| 2009/0266742 | A1 | 10/2009 | Newman et al. |
| 2012/0253079 | A1 * | 10/2012 | Weber ............... C07C 45/512 568/403 |

OTHER PUBLICATIONS

PCT Written Opinion issued in corresponding PCT Application No. PCT/US2013/038780 on Jul. 15, 2013 (6 pp.).
Francis T.S. Yu et al., "Fiber Optic Sensors", (2002).
Tait et al., Measurement of the Temperature of Burning Particles in Fluidized Beds, CHEMECA 86, Adelaide, pp. 156-160, (1986).
Linjewile et al., "Optical Probe Measurements of the Temperature of Burning Particles in Fluidized Beds", Fuel, 1994, vol. 73, No. 12, pp. 1880-1888.
Quarterly Technical Progress Report—Report No. 1, "Laser Ultrasonic Furnace Tube Coke Monitor", US Department of Energy, 1998.

* cited by examiner

METHOD TO OPTIMIZE RUN LENGTHS AND PRODUCT QUALITY IN COKING PROCESSES AND SYSTEM FOR PERFORMING THE SAME

BACKGROUND OF THE INVENTION

1. Field

The field of the disclosed subject matter is detection of coking in refinery equipment. More specifically, the field of the disclosed subject matter is the use of optical sensing networks to detect coking in refinery equipment.

2. Description of Related Art

The processing of a hydrocarbon-containing feed streams at elevated temperatures in a processing zone, such as a furnace, heat exchanger, distillation tower or other refinery equipment, can result in the formation of carbonaceous substances which can deposit on surfaces of the equipment. Such carbonaceous substances are generally referred to as "coke" in the fields of petroleum refining and petro-chemical processes.

Coke deposition on equipment surfaces can alter the operation of the equipment, usually in an undesirable manner. For example, feed streams are heated in a furnace before being introduced to distillation columns. Formation of coke can result in a blockage of tubes in the furnace, as well as the blockage in the transfer lines from the furnace to the distillation column. Additionally, coking often occurs in the column itself, typically within wash beds or at interfaces between different types of packing or the like. Coke can also occur in the bottom of the tower and plug liquid outlets and pump strainers, causing pump cavitation and damage.

After the process of distillation and vacuum distillation, petroleum refining operations in which crude oil is processed frequently produce residual oils. Many oil refineries recover valuable products from heavy residual hydrocarbons. Residual oil, when processed in a delayed coker, is heated in a furnace to a temperature sufficient to cause destructive distillation. In this manner, a substantial portion of the residual oil is converted, or "cracked" to usable hydrocarbon products and the remainder yields petroleum coke, a material composed mostly of carbon.

Generally, the delayed coking process involves heating the heavy hydrocarbon feed from a fractionation unit, then pumping the heated heavy feed into a large steel vessel commonly known as a coke drum. Coking typically begins in a furnace, continues in a transfer line, and finishes in the coke drum. The delayed coking process employs a furnace that operates at temperatures as high as about 1000° F., roughly 50 to 100° F. higher than the operating temperature of the coke drum. The high furnace temperatures can promote the rapid formation of insoluble coke deposits on the furnace tubes and transfer lines.

When coke deposits reach excessive levels, the operation must be shut down and the furnace de-coked. Frequent interruptions for cleaning can lead to high operating costs due to increased amounts of time the operation is off-line, in addition to the cost of the de-coking operations.

The chemical and physical factors involved in the formation of coke have not been fully elucidated. That is, the propensity of certain feed streams to form coke and the rate at which coke is actually formed and deposited in industrial plant such as petroleum refineries and petrochemical works is not currently predictable. As a result, maintenance schedules which take account of deterioration in process and equipment performance due to coke are not necessarily accurate or efficient. Hence, there is a need to detect and to predict coking in refinery equipment or the like.

Detection of coking in refinery equipment, including distillation towers, distillation tower bottom circuits, distillation tower feed furnaces, and coker feed furnaces and transfer lines, has been addressed with a variety of techniques. For example, measurement of pressure drop has been used to detect coking. This technique has been problematic, such as for vacuum tower wash beds, where the pressure drop is typically only on the order of a few mmHg in these wash beds when coking occurs. Thus, pressure measurement is highly unreliable. Similarly, temperature differentials between bulk temperatures have also been used to detect coking. However, this technique involves a gross measurement and thus not necessarily accurate.

The use of various external mechanical probes, which measure light emitted by the refinery equipment, for the detection of coking and fouling have been disclosed. For example, in U.S. Pat. No. 4,402,790 (the '790 patent), a mobile machine to gather coke oven flue temperatures is disclosed. The machine includes a probe head attached to an optic cable to transmit infrared radiation to photoelectric detection-conversion cells. The machine also contains a reeling machine for movement of the cable. The probe is manually directed to enter a coke oven flue and the probe head contains viewing ports for the terminal ends of the fiber optic cable to sense infrared radiation. The infrared radiation is transmitted to photoelectric detection-conversion cells for processing to calculate temperature. The machine disclosed is portable and the probe head must be inserted into a coke oven flue to obtain a temperature measurement. Moreover, the machine incorporates an extrinsic fiber optic sensor—that is, infrared radiation from inside the component of refinery equipment is transmitted through the optic cable to photoelectric detection-conversion cells.

By contrast, U.S. patent application Ser. No. 12/024,251, published as US Patent Application Publication No. 2008/0185316, is directed to a mechanical probe with an extrinsic fiber optic sensor to detect light scattering for the detection of flocculation of quench oil. Particularly, U.S. patent application Ser. No. 12/024,251 discloses the use of transmission, reflectance, and attenuated total reflectance probes to detect an increase in light scattering resulting from addition of precipitant to a quench oil sample.

Hence, there remains a need to provide easier and more effective solutions for detecting the advent and progress of coking in refinery equipment in view of the continued desire to provide enhanced mitigation strategies. Furthermore, there remains a need for a detecting system that allows for proactive operations to mitigate coking

SUMMARY OF THE INVENTION

The purpose and advantages of the present application will be set forth in and apparent from the description that follows. Additional advantages of the disclosed subject matter will be realized and attained by the methods, apparatus, and devices particularly pointed out in the written description and claims thereof, as well as from the appended drawings.

In accordance with one aspect of the disclosed subject matter, a system to detect coking in at least one component of refinery equipment is provided. The system includes a fiber optic assembly having at least one optical fiber operably coupled with the component of refinery equipment. The fiber optic assembly further includes an electromagnetic radiation source, such as a light source, to transmit electromagnetic radiation having a known parameter through the optical fiber and a receiver to receive the electromagnetic radiation from the optical fiber. The system also includes a processor in communication with the fiber optic assembly to identify a shift in the electromagnetic radiation parameter received by the receiver, the shift corresponding to an operating characteristic of the component which can include the structure of and/or the process fluid within the component, separately or in combination.

For purpose of reference and not limitation, the electromagnetic radiation source described herein is a light source to transmit light in at least a portion of the ultraviolet, visible and infrared spectrum. In one embodiment, the optical fiber extends continuously between the light source and the receiver. Here, the light source and the receiver can be on opposite ends of the optical fiber, such that the receiver receives transmitted light, or the light source and receiver can be on the same end, wherein the receiver receives reflected and backscattered light. The parameter can include a measure of wavelength, intensity, phase, or polarization of the light and the operating characteristic can include a measure of process fluid temperature, opacity, density and composition and/or a measure of the component structure temperature, strain and surface condition. For example, in one embodiment, the parameter received by the receiver is wavelength and the operating characteristic is temperature.

In another embodiment, the optical fiber has a gap defined therein between the light source and the receiver, the gap being disposed within a portion of the component. For example, the optical fiber can include a first optical fiber segment having a first terminal end and a second optical fiber segment having a second terminal end, the first terminal end being aligned with and fixed in a spaced relationship from the second terminal end to define the gap therebetween (i.e., the distal end of the first optical fiber segment being aligned and separated in a fixed spatial relationship with the proximal end of the second optical fiber segment). In this embodiment, for purpose of illustration and not limitation, the parameter received by the receiver can be intensity and the operating characteristic can be density of particulates in the process fluid. Alternatively, for example, the parameter received can be a light wavelength spectrum with the wavelengths tuned to detect various molecules known to be precursors of coke material.

In another embodiment of the disclosed subject matter, the fiber optic assembly includes a plurality of optical fibers in communication with the light source and the receiver. In one embodiment, the plurality of optical fibers can be operatively coupled with a plurality of portions of the same component. In an alternative embodiment, the plurality of optical fibers are operatively coupled with a plurality of components of the refinery equipment.

The system to detect coking can further include a controller coupled with the processor to initiate an operation in response to the shift in the parameter received by the processor. For example, the operation can include preventative measures such as rapid wash cycles, changes in the spatial distribution of the wash fluid, a reduction in operating temperature of the component, adjusting heat fluxes in the component, or introducing coil injection steam pulsing in the component. Additional or alternative operations also can be used, and are not limited to those described above.

In accordance with another aspect of the present invention, a method of detecting coking is provided. The method includes providing a fiber optic assembly including at least one optical fiber, the fiber optic assembly further including an electromagnetic radiation source, such as a light source, to transmit electromagnetic radiation having a known parameter through the optical fiber and a receiver to receive the electromagnetic radiation from the optical fiber. The method further includes operably coupling the fiber optic assembly with at least one component of refinery equipment. For example, but not limitation, the fiber optic assembly can be coupled by a transition interface or feedthrough flange outside of the component at ambient conditions to the optical fiber in the interior of the component at process conditions of temperature, pressure, and fluid composition). The method further including identifying a shift in the parameter received by the receiver; and determining a corresponding operating characteristic of the component.

The subject matter disclosed herein can enable the early detection of the coking and coke precursors, as well as enable better understanding of the cause of coking in the component—for example, whether the initial coking is always in the highest temperature location, or whether the initial formation is due to loss of liquid wetting or the like.

BRIEF DESCRIPTION OF THE DRAWINGS

The disclosed subject matter will now be described in conjunction with the accompanying drawings in which.

DETAILED DESCRIPTION OF THE INVENTION

Reference will now be made in detail to embodiments of the disclosed subject matter, examples of which are illustrated in the accompanying drawings. The disclosed subject matter presented herein are generally directed to systems and methods for detecting coking. For purposes of illustration and understanding, exemplary embodiments of the system and method of the disclosed subject matter will be described in conjunction with each other.

As used herein, the term "light" is intended to include electromagnetic radiation at least in all or a portion of the infrared, visible, and/or ultraviolet spectrum.

In accordance with one aspect of the disclosed subject matter, a system to detect coking in at least one component of refinery equipment. The system includes a fiber optic assembly having at least one optical fiber operably coupled with the component of refinery equipment. The fiber optic assembly further includes a light source to transmit light having a known parameter through the optical fiber and a receiver to receive the light from the optical fiber. The system includes a processor in communication with the fiber optic assembly to identify a shift in the parameter received by the receiver, the shift corresponding to an operating characteristic of the component.

Figure 1:
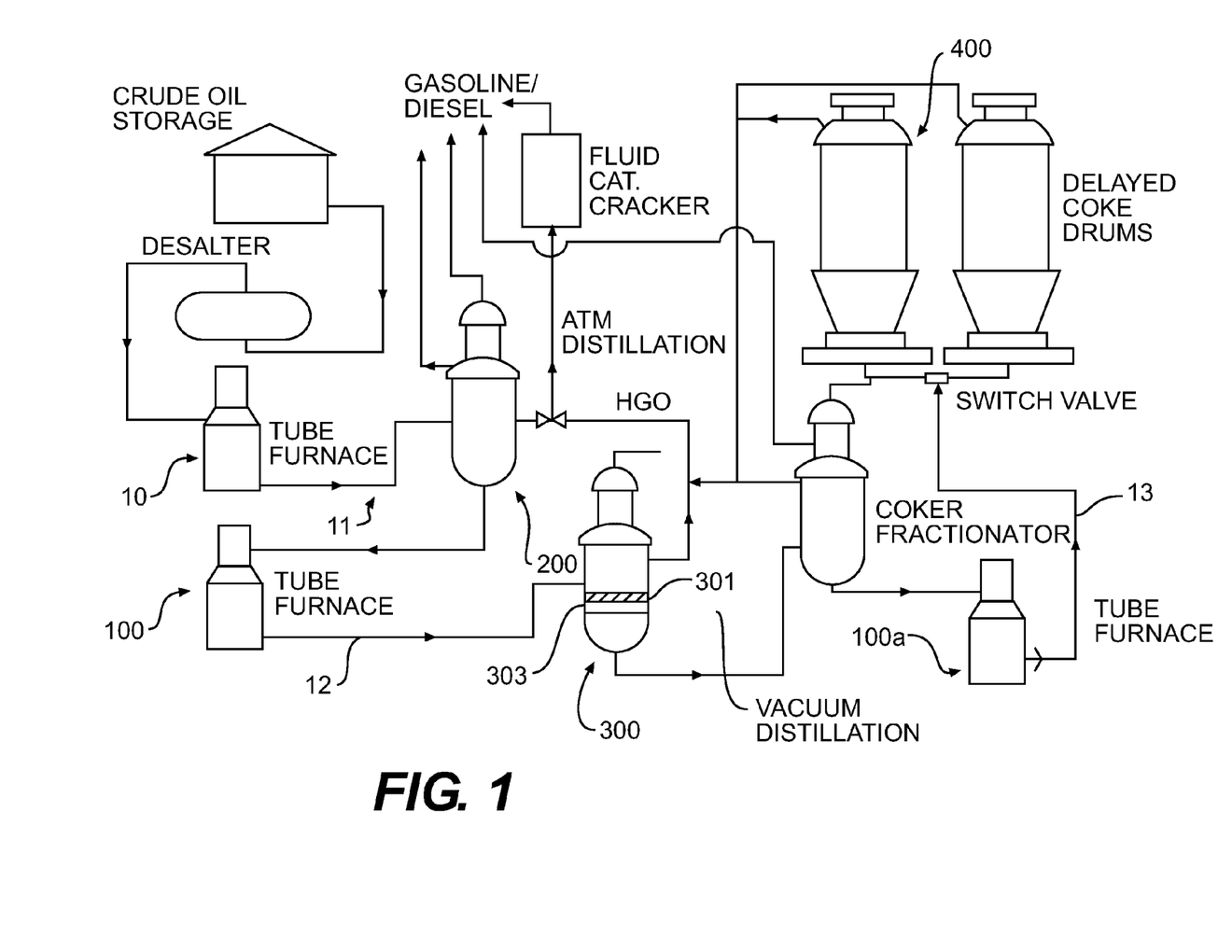
FIG. 1 is a schematic diagram of a representative embodiment of refinery equipment.

For purpose of illustration and not limitation, reference is made to a representative embodiment of a conventional refinery as shown in FIG. 1. As depicted, refinery equipment includes an array of components. Coking can occur throughout the equipment in a number of discrete locations or components. For example, and not limitation, conventional refinery equipment generally includes, but is not limited to, a coker feed furnace 100a, a vacuum distillation tower 300, a vacuum distillation tower feed furnace 100, an atmospheric distillation tower 200, an atmospheric distillation tower feed furnace 10, a transfer line (11, 12 or 13), a wash bed 303, and packing layers 301. The component of refinery equipment is not limited to the components presently listed, as one skilled in the art would recognize that any suitable component can be provided. For example, the component of refinery equipment for the system and method as disclosed herein can be any component of refinery equipment wherein coking occurs.

With reference to FIG. 1 the process of refining crude oil generally includes heating of a feed stream in a furnace 10, transferring the feed stream through a transfer line 11 to an atmospheric distillation column 200. The furnace 10 can be a tube furnace having a furnace tube 101. Coking can occur in the furnace tube 101, the transfer line 11, or in the atmospheric distillation column 200. The process typically continues by transferring residual oils from the atmospheric distillation column 200 to a vacuum distillation tower feed furnace 100, through a transfer line 12, and to a vacuum distillation tower 300. The vacuum distillation tower feed furnace 100 can contain a furnace tube 101. Coking can also occur in any of these components. Many refineries continue the refining process by transferring residual oils from the vacuum distillation tower 300 to a coker feed furnace 100a, through a transfer line 13 and into a delayed coker arrangement 400. The coker feed furnace 100a can be a tube furnace having a furnace tube 101. Coking can occur in any of these components as well. A more detailed description of conventional refinery equipment and operations is disclosed in U.S. Patent Publication No. 2007/0038393, which is incorporated by reference in its entirety herein.

As previously noted, the system and method disclosed herein comprise a fiber optic assembly having at least one optical fiber operably coupled with a component of the refinery equipment, as well as a light source and a processor in communication with the optical fiber.

Generally, the fiber optic system operates under the principle of total internal reflection. Fiber optic sensors can be grouped into two broad categories: extrinsic fiber optic sensors and intrinsic fiber optic sensors. An extrinsic fiber optic sensor generally operates by emitting light into an environment, whereby a parameter of the light beam is modulated externally from the fiber by a characteristic of the environment. With an intrinsic fiber optic sensor, an environmental characteristic affects the parameter of the light beam while the light is still in the fiber itself.

For example, for an extrinsic fiber optic sensor, a light source transmits light through the fiber with one or more known parameters, such as a measure of wavelength, intensity, phase, or polarization. An extrinsic sensor arrangement can have an input fiber and an output fiber. The light passes through the input fiber and into an environment, and then into the output fiber. Alternatively, an extrinsic sensor arrangement can have one fiber that acts both as the input fiber and the output fiber. The parameter of the light is modified by a characteristic of the environment, such as temperature, opacity, density or composition. The light with modified parameter travels through the output fiber to a receiver, and the shift or differential of the known parameter can be measured by the receiver and correlated to the environmental condition.

For an intrinsic fiber optic sensor, a light source transmits light with a known parameter through a fiber. With the fiber exposed to the environment, the environmental characteristic modifies the known parameter of the transmitted light within the fiber. The light is then received by a receiver to measure the parameter of the received light. The receiver can be configured to receive light transmitted through the optical fiber, or reflected or scattered back—that is, the fiber can span continuously between the light source and the receiver, or the receiver and light source can be coupled to the same terminal end of the fiber. As with the extrinsic fiber optic sensor, the shift or differential in the known parameter can be measured and correlated to the external condition. Additional details and description of the operating principles of a fiber optic system are disclosed in FRANCIS T. S. YU ET AL., FIBER OPTIC SENSORS (2002), which is incorporated by reference in its entirety herein.

The corresponding features for the fiber optic assembly are available and can be selected for the operating parameters of the refinery equipment. Examples include the use of an extrinsic fiber optic sensor assembly for measuring opacity in an environment enclosed by a component of refinery equipment or the use of an intrinsic fiber optic sensor assembly for measuring temperature in a component of refinery equipment. Many alternative fiber optic sensor assemblies and arrangements can be used for corresponding operating parameters.

With reference to FIGS. 2-6, various embodiments of a fiber optic assembly are depicted. As shown in each embodiment, for purpose of illustration and not limitation, at least one optical fiber (150, 350) is operably coupled with the component of refinery equipment. The fiber optic assembly further includes a light source 501 to transmit light having a known parameter through the optical fiber (150, 350) and a receiver 502 to receive the light from the optical fiber (150, 350). The system as shown schematically includes a processor 500 in communication with the fiber optic assembly to identify a shift in the parameter received by the receiver, the shift corresponding to an operating characteristic of the component.

Figure 2:
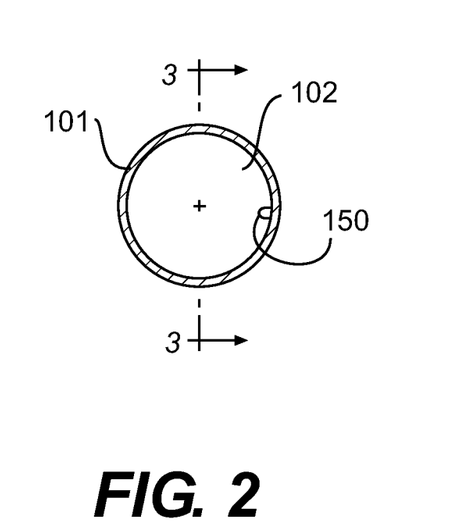
FIG. 2 is a cross-sectional end view of a conventional refinery tube, illustrating one embodiment of the system to detect coking described herein having an optical fiber aligned along an inside wall of the tube.
Figure 3:
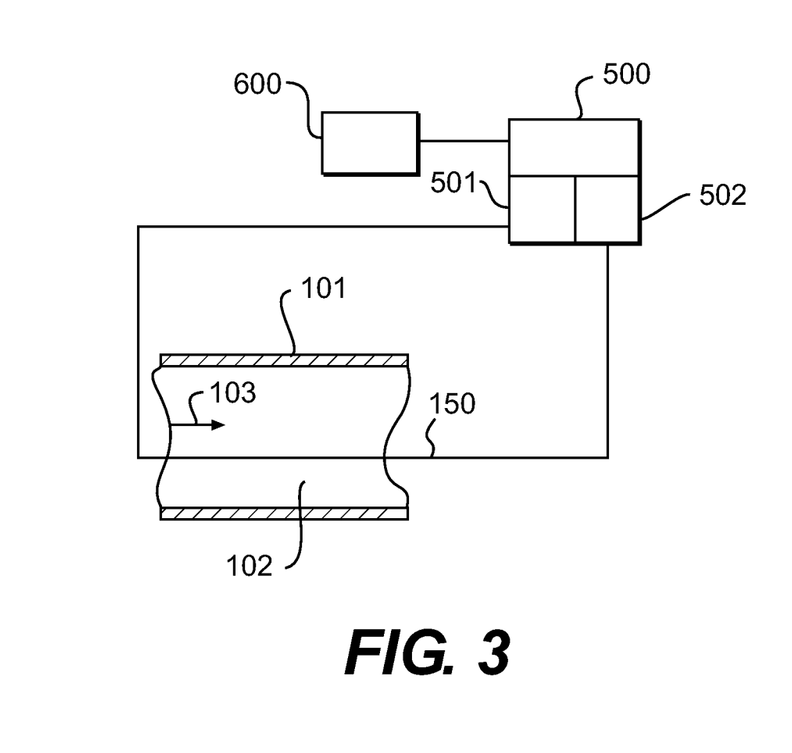
FIG. 3 is a cross-sectional side view of the tube of FIG. 2 at line 3-3, with a schematic representation of the fiber optic assembly disclosed herein.

With reference to the embodiment of FIG. 2 and FIG. 3, the optical fiber (150) can extend continuously between the light source 501 and the receiver 502. FIG. 3 depicts the optical fiber 150 extending from light source 501, through the component of refinery equipment, and then to receiver 502. In this manner, receiver 502 receives light transmitted through optical fiber 150. Alternatively, it is recognized that the light source and receiver can be on the same end of the optical fiber, such that the receiver receives light reflected or backscattered from a terminal end of the optical fiber. For example with reference to FIG. 2, the optical fiber 150 is aligned along the inside wall of a furnace tube 101 contained in a feed furnace (10, 100, 100a). Often coking in a furnace tube 101 occurs along the wall and continues to build radially towards the center 102 of the tube. The coking along the inner wall surface will insulate the tube wall from the fluid flowing therethrough illustrated by 103 in FIG. 3. As such, heat transfer to the fluid will be reduced and the wall of the tube will heat up because it is heated externally in the furnace.

The optical fiber 150 aligned along the tube wall can be used to detect an increase in temperature at the wall. For example, the increase in temperature along the wall of the tube will impact one or more parameters of the light transmitted through the optical fiber. This shift in the known parameter can be measured by the processor, once received by the receiver, and then used to determine the temperature measured along the optical fiber. That is, the shift in wavelength has a known or predetermined relationship or function with temperature. This predetermined relationship or function can be established mathematically or by calibration. Similarly, other known direct relationships or functions given a known parameter and characteristic can be calibrated or otherwise known. Hence, this approach is applicable to any of a number of components of the refinery equipment, not just feed furnaces (10, 100, 100a) and for the measure of a variety of parameters and corresponding operating characteristics. Additionally, one of ordinary skill in the art will recognize that the optical fiber 150 may be aligned along the outside wall of the furnace tube 101 if suitably insulated for accurate measurement, as well as additional arrangements.

Figure 4:
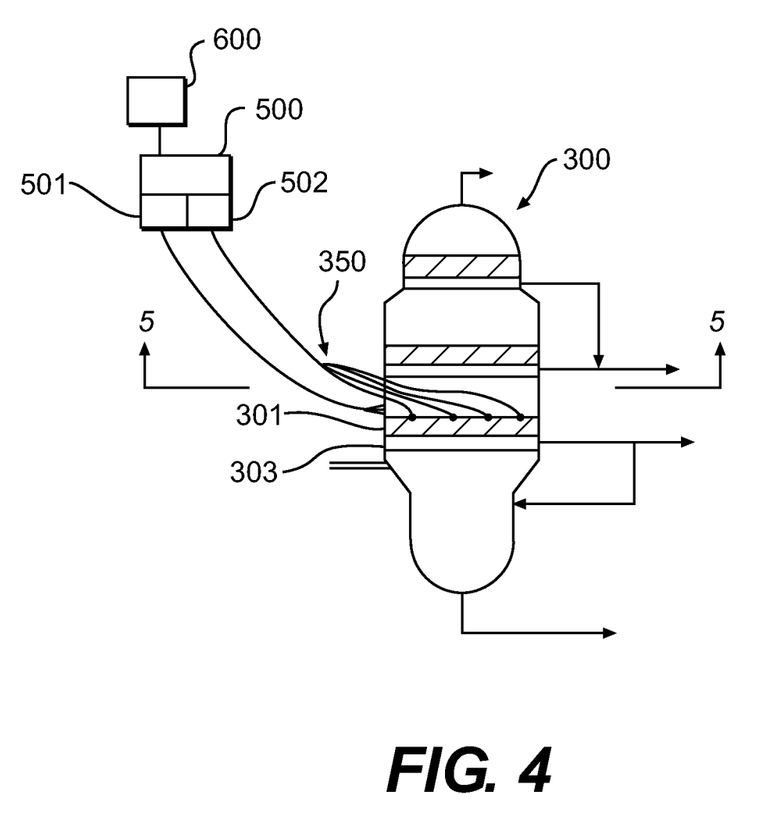
FIG. 4 is a schematic representation of a vacuum distillation tower, illustrating one embodiment of the system to detect coking described herein including a plurality of optical fibers operatively coupled with a packing layer within the vacuum distillation tower described herein.
Figure 5:
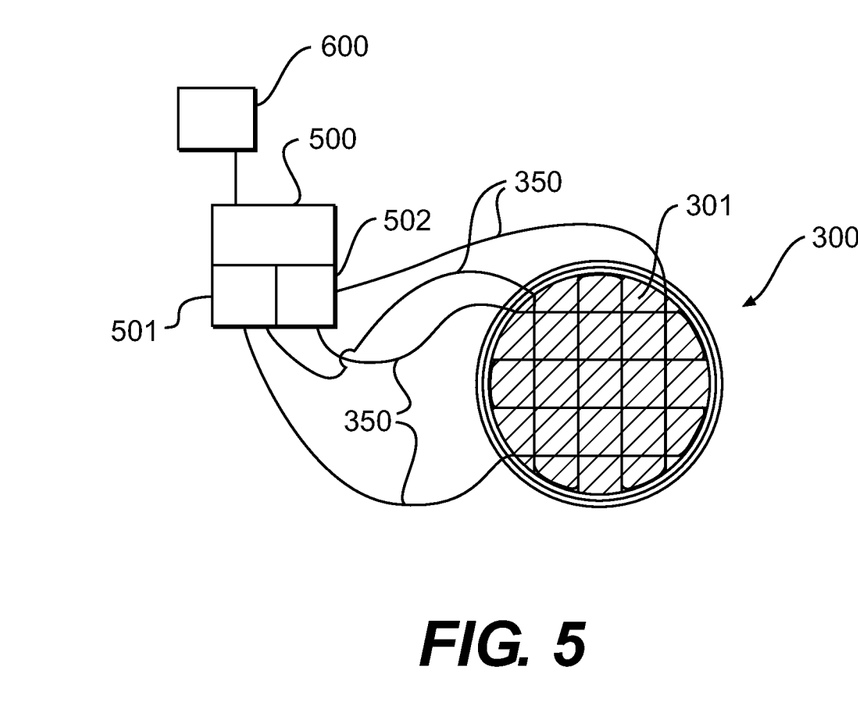
FIG. 5 is a cross-sectional plan view of the vacuum distillation tower of FIG. 4 at line 5-5, with a schematic representation of the fiber optic assembly disclosed herein.

In some embodiments the fiber optic assembly includes a plurality of optical fibers in communication with the light source and the receiver. As shown in FIGS. 4-5, plurality of optical fibers 350 can be operatively coupled with a plurality of portions of the same component 301. Alternatively, the plurality of optical fibers can be operatively coupled with different components of the refinery equipment. For the purpose of illustration and not limitation, FIG. 4 and FIG. 5 show a vacuum distillation tower 300 having a packed wash bed 301 and a spent wash draw tray 303. The plurality of optical fibers 350 operatively coupled within the packed wash bed 301 generally to form a grid or array. In distillation towers, coking often occurs in wash beds. For example, coking can occur at the middle of the bed or at interfaces between different packing layers. Hence, coking can be detected across the plane by arranging a plurality of fiber optic cables between, or on, the packing layers. One of ordinary skill in the art will recognize that there are many suitable arrangements for the plurality of optical fibers 350. For example, one or more optical fibers 350 can be aligned in a spiral form, or a series of concentric circles. Additionally, or alternatively, one or more optical fibers can be arranged, each with a terminal end at a desired location to reflect or scatter light back to the receiver as previously described.

In accordance with another embodiment, the optical fiber can have a gap defined therein between the light source and the receiver, with the gap being disposed within a portion of the component. For example, and with reference to FIG. 6, the optical fiber can include a first optical fiber segment 601 having a first terminal end 603 and a second optical fiber segment 602 having a second terminal end 604, the first terminal end 603 being aligned with and fixed in a spaced relationship from the second terminal end 604 to define the gap therebetween. The first terminal end and second terminal end can be fixed in place with an external supporting mechanism 600. In this embodiment, a known amount of light would be transmitted across the gap if the environment in the component were fully transparent. In this manner, when opacity is increased in the environment in the component, for example, by the dissolution or entrainment of resid particulates, the light transmitted through the gap would be attenuated. The amount of attenuation in light is measured once received by the receiver, and then correlated by the processor to determine the operating condition of the component, such as the amount of particulate or the composition of the fluid in the gap by spectrographic analysis.

One of ordinary skill in the art will recognize that the embodiments depicted in FIGS. 2-6 are exemplary embodiments, and thus there are a number of additional arrangements possible. For example, the light source and the receiver can be coupled at the proximal end of the optical fiber, where the light received by the receiver is the product of Raman or Rayleigh backscattering of incident light from the light source or from fluorescence from the process fluid if the distal end of the fiber is in the process fluid.

Figure 6:
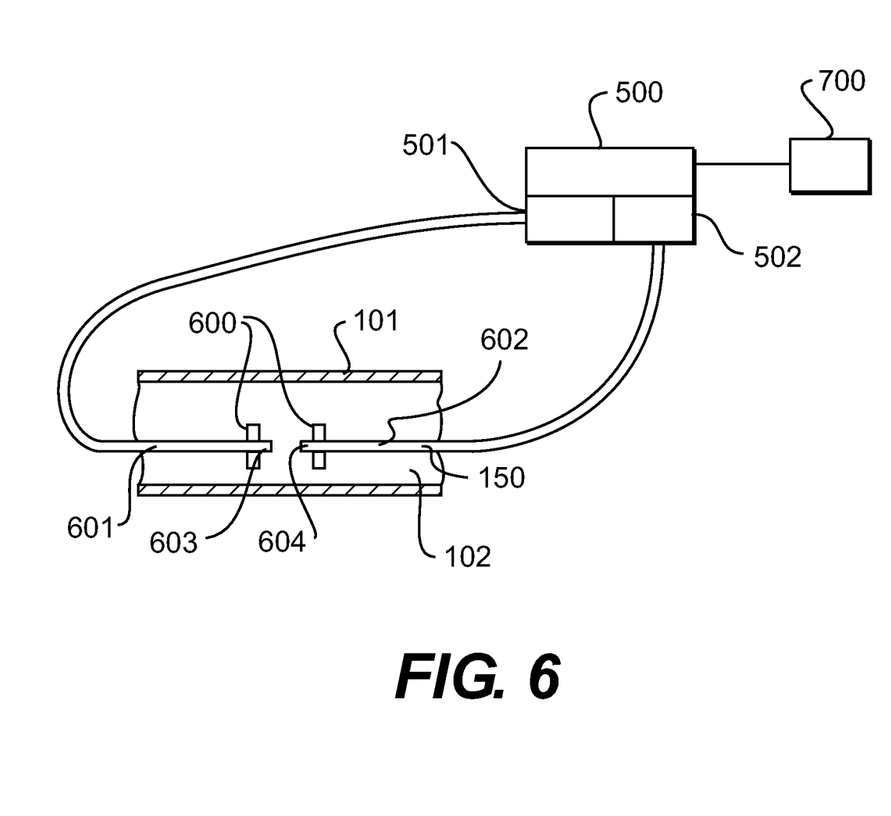
FIG. 6 is a cross-sectional side view of a conventional refinery tube, illustrating one embodiment of the system to detect coking described herein having an optical fiber with a gap defined therein between the light source and the receiver.

In accordance with the system and method disclosed herein, the known parameter of the light transmitted by the light source 501 and received by the receiver 502 can include a measure of wavelength, intensity, phase, or polarization. For example, and with reference to the embodiment shown in FIG. 2 and FIG. 3, the optical fiber extends continuously between a light source 501 and a receiver 502, and the parameter is a measure of wavelength. Similarly, and with reference to the embodiment of FIG. 4 and FIG. 5, the fiber optic assembly includes a plurality of optical fibers 350 in communication with the light source 501 and the receiver 502, and the parameter is wavelength. In an alternative embodiment as depicted in FIG. 6, the optical fiber has a gap defined therein between the light source 501 and the receiver 502 and the parameter is a measure of intensity. One of ordinary skill in the art will recognize that these embodiments are intended as illustration and not limitation, and that there are other suitable combinations of component, fiber optic assembly, and parameter.

As previously noted, a processor 500 in communication with the fiber optic assembly is provided to identify a shift in the parameter received by the receiver 502, the shift corresponding to an operating characteristic of the component. The operating characteristic of the component can include, although not be limited to, a measure of temperature, opacity, density or composition of or within the component. The relationship between the known parameter and the corresponding operating characteristic can be determined mathematically or by calibration. This predefined relationship is stored in the processor for reference as further described.

For example, and with reference to the intrinsic fiber optic embodiments depicted in FIG. 2 and FIG. 3, the operating characteristic is temperature. With the optical fiber 150 aligned along the inside wall of the furnace tube 101, coking will increase the temperature of and along the wall. The optical fiber 150 increases in temperature as a result of being aligned along the interior wall of the furnace tube 101. The light source 501 transmits light having a known wavelength through the optical fiber 150 and the receiver 502 receives the light. A shift in wavelength occurs in the optical fiber 150 because of lattice oscillations induced by increased thermal light. The light transmitted by the energy source 501 interacts with the electrons of the excited molecules and Raman scattering occurs in the optical fiber 150. The processor 500 identifies the shift in the wavelength and correlates the shift corresponding to a change in temperature. Similarly, the processor can detect a shift in the wavelength corresponding to a change in temperature as described with reference to FIG. 2 and FIG. 3. For example, the measure of wavelength can be a measure of wavelength in the infrared spectrum. Alternatively, the measure of wavelength can be a measure of wavelength in the optical spectrum.

Alternatively, and with reference to the extrinsic fiber optic embodiment of FIG. 6, the operating characteristic is opacity or fluorescence of the process fluid within the component, and thus measures of particulate per volume. As previously noted, the optical fiber has a gap defined therein between the light source 501 and the receiver 502, the gap being disposed within a portion of packing layers. In this embodiment, where the environment in the component process fluid is fully transparent, the gap would transmit a known amount of light provided by the light source. Opacity is increased through the entrainment of resid particulates. The entrainment of resid particulates and the inability to wash the particulate from the grid can indicate grid coking. The opacity is further increased as the resid particulates form coke and eventually the intensity of the light passing between the gap is completely attenuated. The grid of optical fibers having a gap defined between the light source and the receiver can be arranged at different levels in the wash bed packing or between packing layers or other components. The optical fibers therefore can be used not only to detect coking, but also to detect in-situ compositions and compositional changes.

The system to detect coking can further comprise a display coupled with the processor to display the operating characteristic of the component. For example, and with reference to FIGS. 2-6, the display 700 can be a monitor or the like to present in readable form one or more parameters of the transmitted light and/or characteristics of the component, among other things. Additionally, or alternatively, the display can be a signal or warning to indicate a particular condition that has been reached.

In accordance with respect to another aspect of the disclosed subject matter, the system to detect coking can further comprise a controller coupled with the processor to initiate an operation in response to the shift in parameter received by the processor. For example, the operation can be a preventative measure to address a particular condition corresponding with the related component. The operation can include rapid wash cycles, changes in the spatial distribution of the wash fluid, a reduction in operating temperature of the component, adjusting heat fluxes in the component, or introducing coil injection steam pulsing in the component, or hydroblasting or otherwise removing deposits with high pressure jets of fluid, or washing with a solvent especially selected for enhanced solvency of the deposited material or other operations suitable to address a detected condition. Such enhanced mitigation strategies can allow for continued operation of the refinery equipment with greater recovery of valuable products or extended runlengths. The controller can be included with the processor, as shown, or provided separately.

Any of a variety of known and commercially available elements can be used for the fiber optic assembly described herein, with consideration of the operating environment and required needs. For example, and not limitation, exemplary optical fibers and light sources available from Micron Optics (which provides fiber Bragg grating systems, including the SM125 and SM130), Luna (which provides light scattering based systems, including the Luna DSS 4300), and OZoptics (which provides light scattering based systems).

The present invention has now been described in relation to particular preferred embodiments. However, many other variations and modifications and other uses may be apparent to those skilled in the art such as demonstrated or evident from the various patents and publications identified herein, each of which is incorporated by reference in its entirety. Such variations and modifications are intended to fall within the scope of the following claims.

What is claimed is:

1. A method of detecting coking comprising:
   providing a fiber optic assembly including at least one optical fiber, the fiber optic assembly further including a light source to transmit light having a known parameter through the optical fiber and a receiver to receive the light from the optical fiber;
   operably coupling the fiber optic assembly with at least one component of refinery equipment;
   identifying a shift in the parameter received by the receiver;
   determining a corresponding operating characteristic of the component;
   providing a controller coupled with a processor; and
   initiating an operation in response to the shift in the parameter received by the processor, wherein the operation includes introducing coil injection steam pulsing in the component.

2. The method of claim 1, wherein the operation includes rapid wash cycles.

3. The method of claim 1, wherein the operation includes a reduction in operating temperature of the component.

4. The method of claim 1, wherein the operation includes adjusting heat fluxes in the component.

5. The method of claim 1, wherein the operation includes removing deposits with high pressure jets.

6. The method of claim 1, wherein the operation includes washing with a solvent selected for enhanced solvency of deposited material.

7. The method of claim 1, wherein the operation includes changing distribution of wash fluid.

8. The method of claim 1, wherein the parameter includes a measure of one of wavelength, intensity, phase, and polarization.

9. The method of claim 1, wherein the parameter is a measure of Raman backscattering.

10. The method of claim 1, wherein the parameter is a measure of fluorescence backscattering.

11. The method of claim 1, wherein the parameter is a measure e of wavelength.

12. The method of claim 1, wherein the operating characteristic includes a measure of at least one of temperature, opacity, density, composition and mechanical strain.

13. The method of claim 12, wherein the parameter received by the receiver is wavelength and the operating characteristic is temperature.

14. The method of claim 12, wherein the parameter received by the receiver is intensity and the operating characteristic is the opacity of the fluid within the component.

15. The method of claim 12, wherein the parameter received by the receiver is intensity and the operating characteristic is density of particulate within the component.

16. The method of claim 1, wherein the component includes a vacuum distillation tower.

17. The method of claim 1, wherein the component includes a vacuum distillation tower feed furnace.

18. The method of claim 1, wherein the component includes an atmospheric distillation tower.

19. The method of claim 1, wherein the component includes an atmospheric distillation tower feed furnace.

20. The method of claim 1, wherein the component includes a transfer line.

21. The method of claim 1, wherein the component includes a coker feed furnace.

22. The method of claim 1, wherein the component includes a wash bed.

23. The method of claim 1, wherein the component includes a bottom sump and bottoms liquid outlet of a vacuum distillation tower.

24. The method of claim 1, wherein the component includes a layer of packing.

* * * * *